United States Patent [19]

Throckmorton

[11] 4,410,461
[45] Oct. 18, 1983

[54] PRODUCTION OF BENZYLIC ESTERS
[75] Inventor: Peter E. Throckmorton, Plain City, Ohio
[73] Assignee: Ashland Oil, Inc., Ashland, Ky.
[21] Appl. No.: 303,646
[22] Filed: Sep. 18, 1981
[51] Int. Cl.$^3$ .......................... C11C 3/04; C09F 5/08; C07C 67/00
[52] U.S. Cl. .................................. 260/410; 260/406; 260/410.5; 560/193; 560/194; 560/231; 560/241
[58] Field of Search ...................... 260/410, 410.5, 406; 560/193, 194, 231, 241; 252/437

[56] References Cited
U.S. PATENT DOCUMENTS 3,547,982 12/1970 McKeon et al. ..................... 560/241
3,772,383 11/1973 Kominami et al. ................. 560/231
4,033,999 7/1977 Onoda et al. ........................ 560/241
4,224,456 9/1980 Umemura et al. .................. 560/241

Primary Examiner—Thomas A. Waltz
Attorney, Agent, or Firm—William Kammerer

[57] ABSTRACT

A catalytic homogeneous liquid phase process for effecting the acyloxylation of toluene to produce the corresponding benzylic ester. The catalyst system comprises Pd(II) and Pb(II) values wherein the palladous element component is associated with a catalytic amount of a tertiary phosphine as a complexed ligand. The indicated catalyst system uniquely facilitates the advantageous use of normally immiscible carboxylic acid reactants for carrying out the underlying benzylic oxidation reaction.

11 Claims, No Drawings

PRODUCTION OF BENZYLIC ESTERS

BACKGROUND OF THE INVENTION

1. Field of the Invention

This invention relates to a catalytic process for effecting the benzylic oxidation of toluene.

2. Description of the Prior Art

It has hitherto been proposed to prepare benzylic esters by the acyloxylation of an appropriate aromatic hydrocarbon either in the vapor or liquid phase. Since the underlying reaction involves a benzylic oxidation mechanism, a catalyst is required for carrying out the process. The most effective catalyst for this purpose reported in the prior art is palladium in the form of a palladous compound. It has been further proposed to utilize the palladium catalyst in combination with another compound for the purported purpose of enhancing the activity thereof.

U.S. Pat. No. 3,547,982 is particularly representative of the prior art directed to a liquid phase acyloxylation proces in which the palladium catalyst is modified with a variety of other compounds soluble in the reaction mixture, notably various compounds of tin or phosphorus. More recently in U.S. Ser. No. 029,819, filed Apr. 13, 1979, now abandoned, a co-catalyst system comprised of Pd(II) and Pb(II) values is taught as being especially effective in catalyzing the liquid phase acyloxylation of a variety of compounds having in common an allylic residue.

While the resultant product of the acyloxylation reaction is an ester, the latter only represents a precursor of that which is normally desired; namely, the corresponding alcohol. Consequently, the carboxylic acid reactant essentially amounts to a recycle stream in the process. From the standpoint of convenience, raw material cost and effectiveness, the lower fatty acids and, specifically acetic acid, have been considered as representing the most suitable carboxylic acids for carrying out the process. However, the vapors of the lower fatty acids are extremely corrosive and the use thereof is desirably to be avoided, particularly in any large scale commercial operation considering the substantial amount of recycling involved.

The higher fatty acids as well as a variety of aromatic and acyclic diacids, while substantially noncorrosive in nature, suffer on the other hand, for lacking mutual solubility with the benzylic substrate. In liquid phase homogeneous catalysis reactions in systems where there are a plurality of reactants, it is essential to have the responsive reactants mutually soluble or compatible with one another in order to conduct the reaction in an effective manner. The aforementioned U.S. Ser. No. 029,819, beyond teaching a novel co-catalyst system for the acyloxylation reaction, represents the only known art which addresses the problem of employing a higher fatty acid or applicable diacid in a reaction of this type. Therein it is taught that the requisite homogeneity can be obtained through the use of a coupling solvent in the reaction mixture. Although effective for the purpose indicated, a coupling solvent adds a further cost to the process and undesirably necessitates yet another recycle stream.

SUMMARY OF THE INVENTION

In accordance with the present invention a homogeneous liquid phase process is provided for effecting the benzylic oxidation of toluene whereby the latter is reacted with molecular oxygen and a $C_6$-$C_{18}$ mono- or dicarboxylic acid in the presence of palladium as the intrinsic catalyst species and lead as an extrinsic co-catalyst species with both metals existing in the valence state of two. The indicated homogeneity is attained through the presence of a catalytic amount of a tertiary phosphine in the reaction mixture. The role of the phosphine is that of complexing with the palladous atoms through chemical bonding. The resultant complexes, provided they individually contain at least one phosphine ligand serve to solubilize the palladium in the carboxylic acid medium and facilitate acyloxylation by maintaining homogeneous phase conditions.

DESCRIPTION OF THE PREFERRED EMBODIMENTS

The carboxylic acids useful in the practice of the present invention embrace the spectrum of $C_6$-$C_{18}$ mono- and diacids. As previously indicated the foremost commercial usefulness of the benzylic esters is in the preparation of benzyl alcohol. Thus, for all practical purposes, the carboxylic acid reactant essentially constitutes a recycle stream in the operation of the process. In light of this, there are three main criteria involved in selecting this reactant. These criteria include: capability to provide optimum selectivity with respect to the formation of the ester product, commercial availability of the acid, and thirdly, cost. Accordingly, of the applicable fatty acids, lauric acid represents the acid reactant of preference. Benzoic acid is particularly exemplary of the aromatic mono-acids for use in accordance with this invention.

In the selection of the diacid reactant, another criterion in the forefront is that the acid be a liquid in the operating temperature range and preferably below the preferred operating temperature. There is a significant advantage to using a dicarboxylic acid in that such acids are more polar, lending themselves to being separated from a hydrolysis product with comparative ease. This advantage is evident in a preferred embodiment wherein the benzylic ester is contacted with steam to effect hydrolysis. At the same time the benzyl alcohol is steam distilled from the reaction mixture and the molten acid together with the co-catalyst system recycled to the process. Adipic acid and 1,12-dodecanedioic acid are especially exemplary of the applicable diacids useful in carrying out the indicated preferred embodiment.

The co-catalyst system contemplated herein not only serves to catalyze the underlying oxidation reaction but in addition uniquely functions to maintain the normally immiscible carboxylic acid reactant and the toluene in a homogeneous phase. There is a preferred procedure for combining the various catalyst components and reactants preparatory to effecting the oxidation reaction. This procedure will be amply outlined in the working examples to follow and accordingly the following discussion is primarily addressed to the empirical makeup of the contemplated co-catalyst systems.

The palladous compound will in the course of the reaction equilibrate to form the corresponding salt of the carboxylic acid being utilized. In light of the ready availability and solubility characteristics of palladous acetate such represents the starting compound of choice. Plumbous acetate is likewise preferred as the lead compound. The indicated co-catalyst compounds are combined to provide a palladium to lead atomic ratio of 1:1 to 1:2, respectively. The optional inclusion of an alkali metal soap, preferably that of potassium, serves to improve the acyloxylation conversion rate. Suitable amounts of the supplemental catalyst component is in the order of 1–5 moles thereof per mole of the palladous acetate.

Applicable tertiary phosphines include the triaryl phosphines, the trialkyl phosphines, as well as the various diphosphines of which 1,3-bis(diphenylphosphino) propane is particularly representative. Of the mono phosphines, triphenyl phosphine is preferred. The oxides of the indicated phosphines are functionally equivalent. As a matter of fact the phosphine is converted to the oxide form thereof during the course of the reaction. The phosphine is broadly included in the co-catalyst systems on the basis of 1–6 moles per atom of the palladous element. The preferred ratio is from 1–4 moles of the tertiary phosphine per atom of the palladous element.

In effecting acyloxylation the reaction mixture is continuously saturated with molecular oxygen. The oxidant gas can be substantially pure oxygen, air, or synthetic mixtures of oxygen and nitrogen. Water generated in the course of the reaction is continuously removed in order to promote the acyloxylation reaction. The applicable range of carboxylic acid to toluene mole ratios is from about 2 to 1, respectively, with 1.5 on the same basis representing the optimal operating ratio. Reaction temperature broadly ranges from about 150°–180° C. with the preferred temperature being in the order of about 160° C.

EXAMPLE I

Oxidation of Toluene to Benzyl Laurate in the Presence of $Pd^{II}/Pb^{II}/Ph_3P$ Catalyst Melted triphenyl phosphine (80°–90° C.) in the amount of 5.5 g was charged to a glass reactor equipped with a reflux condenser, mechanical stirrer, a water-cooled Dean-Stark collector having a heated throat, and a fritted glass tube for introduction of gas below the surface of the reactor contents. Palladous acetate (1.4 g) was stirred into the warm reactor with oxygen slowly bubbling through the triphenyl phosphine until dissolved forming a dark green solution. While maintaining the melt at 60°–90° C., lauric acid (95 g) was introduced to provide a solution of the palladium-phosphine complex. Lead acetate (4.0 g) was then stirred into the clear, dark green, homogeneous solution. The toluene (30 g) was then added, same being conveniently miscible with the preformed catalyst-lauric acid solution. The reaction mixture was heated to reflux while continuously introducing 200 ml/min oxygen. After an induction period of about 1.5 hr of continued oxygenating and heating at reflux, the temperature was raised from 90° to 150° C. in about an hour and then to 160° C. as benzyl laurate (BZL) built up to about 15% wt/wt in the reaction mixture. The reaction mixture remained essentially homogeneous but initially quickly turned from a dark green color, transiently to red and then to a permanent black. The black coloration is due to an equilibrium catalytic amount of colloidally dispersed palladium which in the course of the reaction forms soluble $Pd^{II}$. As reaction proceeded, the water of reaction was continuously removed by collection in the Dean-Stark tube. The reaction was conducted under the conditions noted for about 3 additional hours resulting in the formation of approximately 40% wt/wt benzyl laurate (BZL). Conversion of toluene amounted to 50% whereas the reaction was selective at 96% BZL. Only 2.14 g of loss as $CO_2$ was observed equivalent to 2.1% loss TOL.

EXAMPLE II

Oxidation of Toluene to Benzyl Laurate in the Presence of $Pd^{II}/Pb^{II}/Ph_3P/K^I$ Catalyst To a 2-liter round bottom flask equipped as in Example I were charged in the manner described therein, the following: 27.8 g triphenyl phosphine, 7.07 g palladous acetate, 489 g lauric acid (LA), 20.2 g lead acetate trihydrate, 40 g anhydrous potassium laurate and 150 g toluene. After heating and oxygen blowing of the charge for 4 hours, the temperature was about 160° C. Benzyl laurate (BZL) was then observed by gas chromatography (GC) at 17.5%. Heating at 160° C. for 2.6 additional hours with continued oxygenation at 330 ml/min, $O_2$ (referred to 20° C., 1 atm) resulted in a BZL level of 40.3% as indicated by corrected GC analysis. The retention time was identical to the BZL product of Example I and to an authentic sample. The final composition of the reactor contents of 742 g when the reaction was concluded, after an additional 0.4 hr at 160° C., was indicated by GC to be as follows: 8.3% TOL, 37.6% LA, 39.1% BZL. The remainder was triphenyl phosphine oxide (shown on GC) and catalyst salts (not shown) by difference. Thin layer chromatography indicated no consequential amount of higher boilers was present in the product. Based on these analyses and unchanged toluene condensed in the apparatus, 89.8 g TOL was consumed and 290 g BZL formed, amounting to 100% BZL selectivity of the TOL consumed. Conversion rate was 59% of the TOL charged.

$$\text{Selectivity} = \frac{\text{moles } BZL \text{ formed}}{\text{moles } TOL \text{ consumed}}$$

$$\text{Conversion} = \frac{TOL \text{ consumed}}{TOL \text{ charged}}$$

EXAMPLE III

Oxidation of Toluene to Benzyl Laurate with Simulated Air in the Presence of $Pd^{II}/Pb^{II}/Ph_3P/K^I$ Catalyst To a 500 ml round bottom flask equipped as in Example I, the following were charged according to the procedure described therein: 5.5 g triphenyl phosphine, 1.4 g palladous acetate, 95 g lauric acid (LA), 4.0 g lead acetate trihydrate, 8.0 g anhydrous potassium laurate and 30 g toluene (TOL). As in Example I the dark green clear liquid reaction mixture was oxygenated but with a synthetic mixture simulating air comprising a volumetric ratio of 25% oxygen and 75% nitrogen. The simulated air was bubbled into the reaction at a rate of 200 ml/min at 1 atm (referred to 20° C.). After 6 hrs the temperature reached 160° C. and 19.9% BZL was present in the reaction mixture. After 2.25 hrs additional reaction at 160° C., BZL formation peaked and the indicated GC composition of the reaction mixture was 6.2% TOL, 33.6% LA, 37.9% BZL, the remainder catalyst salts. The conversion of toluene was 54% and 53.4 g BZL formed to result in 96% selectivity. Carbon dioxide formation in the amount of 1.30 g was observed.

EXAMPLE IV

Oxidation of Toluene to Benzyl Laurate in the Presence of $Pd^{II}/Pb^{II}/Ph_2P(CH_2)_3PPh_2/K^I$ Catalyst The procedure of Example I was repeated but substituting an equivalent amount of 1,3-bis(diphenylphosphino) propane for the triphenyl phosphine catalyst, the $Pd^{II}/Pb^{II}/K^I$ catalyst system remaining the same. After 4.8 hrs the temperature was 160° C. and there was 19.4% BZL present. After 5.0 hrs continued reaction at 160° C., there was 34.0% BZL and 4.9% toluene present in the reactor. BZL selectivity based on the toluene accounted for was 98%. Toluene converted was 16.1 g or 54%. Carbon dioxide formation in the amount of 1.18 was observed.

EXAMPLE V

Example II was repeated but with the $Pb^{II}$ co-catalyst component absent. Considerable loss as $CO_2$ was observed (7.06 g $CO_2$ equivalent to 2.1 g TOL loss or 7.0%). The BZL selectivity was diminished to 90%. Toluene conversion was 62%.

EXAMPLE VI

Hydrolysis of Benzyl Laurate Oxidation Product In Situ to Benzyl Alcohol

A reaction product prepared as in Example II in the amount of 86.9 g along with 100 ml distilled water were charged to a pressure reactor. The charge contained 35.6 g (41%) BZL. The charge was heated at 165°–170° C. (450 psig) for 2.25 hrs. Analysis indicated that 22.7 g or 64% of the BZL present was converted to 6.23 g benzyl alcohol (BOH) and 1.87 g benzaldehyde. Total BOH selectivity in the hydrolysis product from the BZL converted was 96%. The hydrolysis product was hot water extracted which upon distillation yielded benzyl alcohol $b_{55mm}114°-120°$ ($n_d^{21°}1.5331$). The infrared spectrogram of the benzyl alcohol product was identical to an authentic sample.

EXAMPLE VII

Distillation of Benzyl Laurate Oxidation Product

Benzyl laurate need not be distilled to provide benzyl alcohol (BOH) as illustrated in the BOH isolation procedure of Example VII. Alternatively, BZL can be readily distilled directly from the crude product under vacuum. A crude benzyl laurate from an oxidation run conducted as described in Example II analyzed by corrected GC 7.3% TOL, 39.7% BZL, 3.1% unknowns and the balance residual catalysts. Vacuum distillation of 138.2 g of said crude through a Claisen distillation head yielded 11.2 g cold-trap volatile liquid, 61.65 g.b. (0.1 mm) 162°–181° C. of a mixture lauric acid (LA)+benzyl laurate (BZL) and 36.92 g. b. (0.1 mm) 181°–193° C. of 76.3% BZL. There was 28.25 g residue containing the catalyst solids, lauric acid, 5% higher boiling unknown and 8.99% BZL. The BZL content totaled 50.75 g, LA 48.85 g and TOL 10.41 g. Since the charge to the oxidation reactor in producing the crude distilled was 27.3 g TOL and 86.48 g LA, TOL conversion was 16.89 g (62%). LA accounted for as equivalent BZL plus distilled LA was 83.85 g (97%). Toluene selectivity to BZL was 96%. The 96% BZL selectivity by distillation (in hand) results may be compared to BZL selectivity 97% by analysis in examples above (GC of crude product). The infrared spectrogram of the distilled benzyl laurate product (BZL) was identical to an unequivocally prepared sample of benzyl laurate.

EXAMPLE VIII

Oxidation of Toluene to Benzyl Dodecandioic Acid Esters in the Presence of $Pd^{II}/Pb^{II}/Ph_3P/K^I$ Catalyst To a ½-liter, round bottom glass reactor equipped as in Example I were charged the following: 3.28 g triphenylphosphine, 2.80 g palladous acetate, 106.3 g dodecanedioic acid (DDA), 4.74 g lead acetate trihydrate and 2.89 g 86% potassium hydroxide. The mixture was stirred and heated to 155° C. providing a homogeneous solution. Oxygen was continuously blown through the solution at 200 ml/min. Heating was continued and as the reactor contents reached 160° C., toluene was pumped into the reactor at an average rate of 0.26 ml/min for 4 hrs. A total charge of toluene of 54.7 g was added to the reactor over the 4 hrs pumping, during which time reactor temperature was maintained at 155°–160° and water was collected in the Dean-Stark tube. The reaction produced 9.78 g water and 0.06 g carbon dioxide. Monobenzyl dodecanedioic acid (MBZD) and dibenzyldodecane dioate (DBZD) products were produced and were observed in the reactor contents (168 g) by gas chromatography (GC) at levels of 49.3% and 5.0% by weight MBZD and DBZD, respectively. The GC retention times ($R_f$) of these observed products were identical to the $R_f$ of authentic samples. The balance of the reactor contents was by GC analysis 11.4% toluene, 15.6% dodecanedioic acid and 1.6% unidentified. There was left 17.1% of the charge as non-volatile catalyst salts, potassium salt and any other not chromatographed. Based on the above GC results and the net toluene consumed (net TOL=54.7 g−free TOL in reactor−TOL in exit cold trap=28.7 g), the conversion of toluene was 53% and total benzyl selectivity was 96% (83% to MBZD plus 13% to DBZD).

The conversion and selectivities in this example were calculated by the following equations:

$$MBZD \text{ Selectivity} = \frac{\text{mols } MBZD \text{ found}}{\text{mols } TOL \text{ consumed}}$$

$$DBZD \text{ Selectivity} = \frac{2 \times (\text{mols } DBZD \text{ found})}{\text{mols } TOL \text{ consumed}}$$

$$\text{Conversion} = \frac{TOL \text{ consumed}}{TOL \text{ charged}}$$

The identity of the toluene oxidation products as mono- and di-benzyl dodecanedioic acid esters was aided by comparing the infrared spectrograms of petroleum ether and ethyl ether extracts of the oxidation reactor product with the spectrograms of the authentic esters. The spectral absorption bands for benzyl ester and carboxyl groups were superposable between the oxidation products and the knowns. The bands were as follows: 3200 (broad), 1710 cm$^{-1}$: COOH; 1735: COOCH$_2$Ph; 1605, 1585 cm$^{-1}$: Aromatic and 1465, 1455 cm$^{-1}$: CH$_2$. The hot petroleum ether extract of the oxidation reaction on evaporation yielded by weight 20% of raw product as DBZD-rich product ester. Normalized to avoid some higher product, the GC analysis was: 6% DDA, 19% MBZD, 57% DBZD and the balance (18%) unidentified. The hot ethyl ether extract of the oxidation reaction on evaporation yielded about 40% by weight raw product as MBZD-rich product ester. The GC analysis was: 11% DDA, 86% MBZD, 1% DBZD and the balance (2%) unidentified. Benzyl alcohol product was then steam distilled from the benzyldodecanedioic ester by introducing superheated steam into the melt at 200° C. Dodecanedioic acid was co-produced suitable for recycle to the oxidation reactor.

EXAMPLE IX

Oxidation of Toluene to Benzyl Adipic Acid Esters Using $Pd^{II}/Pb^{II}/Ph_3P$ Catalyst To a reactor equipped as in Example VIII was charged the following: 3.28 g triphenylphosphine, 2.80 g palladous acetate, 66.64 g adipic acid and 4.74 g lead acetate trihydrate. The mixture was stirred and heated to 155° to a homogeneous solution. Oxygen was continuously blown through the solution at 100 ml/min. Heating to 160° C., toluene was pumped into the reactor at an average rate of 0.21 ml/min for 5.45 hrs. A total charge of toluene of 60.0 g was added to the reactor, during which time temperature was maintained at 150°–160° and water was collected in the tube. The reaction produced 11.25 g water and 2.11 g $CO_2$. Monobenzyl adipic acid (MBZD) and dibenzyl adipate (DBZA) products were produced and observed in the reactor contents (124 g) by GC. The GC selection times ($R_f$) of these observed products were identical to $R_f$ of authentic samples. The complete GC analysis of the reactor contents was as follows: 32.2% MBZA, 14.1% DBZA, 10.8% toluene, 20.8% adipic acid, 3.9% benzoic acid, 3.9% dibenzyl ether and 4.8% of unknown composition. The balance, 9.5% not chromatographable by GC, was the catalyst materials of the charge, which at the reaction finish comprised non-volatile palladium and lead complexes and the combined triphenylphosphine.

Based on the above GC results and the net toluene consumed (net TOL=53.4 g — free TOL in reactor — TOL in exit cold trap=34.3 g), the conversion of toluene was 64% and total benzyl selectivity calculated on a molar basis as in Example VIII above was 88% (46% to MBZA plus 29% to DBZA and 13% to dibenzyl ether). The adipic esters along with the dibenzyl ether product formed may be steam—hydrolyzed to benzyl alcohol.

The identity of the toluene ester products as mono- and di-benzyl adipic acid esters (MBZA/DBZA) as well as the identity of the dibenzyl ether product was confirmed by comparing GC retentions and infrared spectra of authentic samples. The known esters were prepared by unambiguous syntheses. The infrared bands of the MBZA/DBZA esters product, were observed as follows: 3200 (broad), 1705 $cm^{-1}$; COOH; 1730 $cm^{-1}$ $COOCH_2Ph$; 1605, 1585 $cm^{-1}$: Aromatic and 1450, 1455 $cm^{-1}$: $CH_2$. The bands were identical to the infrared bands of the knowns. The hot toluene extract of the crude product by boiling with toluene and then decanting from the insoluble residue of catalysts, yielded on evaporation 100% of the organic reaction product produced.

What is claimed is:

1. A homogeneous liquid phase benzylic oxidation process which comprises reacting toluene, a $C_6$–$C_{18}$ mono- or dicarboxylic acid and molecular oxygen in the presence of a catalytic amount of an organic soluble Pd(II)-Pb(II) co-catalyst system wherein the respective palladous atoms are complexed with at least a mole of a tertiary phosphine.

2. A homogeneous liquid phase benzylic oxidation process which comprises reacting toluene, a $C_6$–$C_{18}$ mono- or dicarboxylic acid and molecular oxygen in the presence of a catalytic amount of an organic soluble Pd(II)-Pb(II) co-catalyst system wherein the respective palladous atoms are complexed with at least a mole of a tertiary phosphine, said co-catalyst system further including from about 1 to 5 moles of the potassium salt of said mono- or dicarboxylic acid reactant per atom of the palladous element.

3. The process in accordance with claim 1 or 2 wherein the respective palladous atoms are complexed with 1-4 moles of a tertiary phosphine.

4. The process in accordance with claim 3 wherein said carboxylic acid is lauric acid.

5. The process in accordance with claim 4 wherein said tertiary phosphine is triphenyl phosphine or 1,3 bis(diphenyl phosphino) propane.

6. The process in accordance with claim 3 wherein said carboxylic acid is benzoic acid.

7. The process in accordance with claim 6 wherein said tertiary phosphine is triphenyl phosphine or 1,3-bis(diphenyl phosphino) propane.

8. The process in accordance with claim 3 wherein said carboxylic acid is 1,12-dodecanedioic acid.

9. The process in accordance with claim 8 wherein said tertiary phosphine is triphenyl phosphine or 1,3-bis(diphenyl phosphino) propane.

10. The process in accordance with claim 3 wherein said carboxylic acid is adipic acid.

11. The process in accordance with claim 10 wherein said tertiary phosphine is triphenyl phosphine or 1,3-bis(diphenyl phosphino) propane.

* * * * *